(12) United States Patent
Singh

(10) Patent No.: US 9,321,780 B2
(45) Date of Patent: Apr. 26, 2016

(54) BUPRENORPHINE DIMER AND ITS USE IN TREATMENT OF GASTROINTESTINAL DISORDERS

(71) Applicant: OrphoMed LLC, Mill Valley, CA (US)

(72) Inventor: Nikhilesh Nihala Singh, Mill Valley, CA (US)

(73) Assignee: OrphoMed, Inc., Mill Valley, CA (US)

(*) Notice: Subject to any disclaimer, the term of this patent is extended or adjusted under 35 U.S.C. 154(b) by 0 days.

(21) Appl. No.: 14/697,174

(22) Filed: Apr. 27, 2015

(65) Prior Publication Data

US 2015/0307504 A1 Oct. 29, 2015

Related U.S. Application Data

(60) Provisional application No. 61/985,207, filed on Apr. 28, 2014, provisional application No. 62/101,768, filed on Jan. 9, 2015, provisional application No. 62/176,883, filed on Jan. 9, 2015.

(51) Int. Cl.

| | | |
|---|---|---|
| A61K 31/485 | (2006.01) | |
| C07D 489/12 | (2006.01) | |
| C07D 489/02 | (2006.01) | |
| C07C 217/64 | (2006.01) | |
| C07C 217/70 | (2006.01) | |
| C07C 233/43 | (2006.01) | |
| C07D 489/08 | (2006.01) | |
| A61K 31/137 | (2006.01) | |
| A61K 31/167 | (2006.01) | |
| C07C 233/16 | (2006.01) | |
| C07D 489/00 | (2006.01) | |
| C07C 233/25 | (2006.01) | |

(52) U.S. Cl.
CPC ............ *C07D 489/02* (2013.01); *A61K 31/137* (2013.01); *A61K 31/167* (2013.01); *A61K 31/485* (2013.01); *C07C 217/64* (2013.01); *C07C 217/70* (2013.01); *C07C 233/16* (2013.01); *C07C 233/25* (2013.01); *C07C 233/43* (2013.01); *C07D 489/00* (2013.01); *C07D 489/08* (2013.01); *C07C 2101/14* (2013.01)

(58) Field of Classification Search
USPC ............................................ 514/279; 546/39
See application file for complete search history.

(56) References Cited

U.S. PATENT DOCUMENTS

| | | | |
|---|---|---|---|
| 3,896,235 | A | 7/1975 | Harfenist |
| 7,056,500 | B2 | 6/2006 | Bentley et al. |
| 7,084,150 | B2 | 8/2006 | Boer et al. |
| 7,759,358 | B2 * | 7/2010 | Crooks et al. .................. 514/282 |
| 8,063,059 | B2 | 11/2011 | Herman |
| 8,183,376 | B2 | 5/2012 | Cheng et al. |
| 8,461,171 | B2 | 6/2013 | Holaday et al. |
| 8,617,530 | B2 | 12/2013 | Roberts et al. |
| 8,962,647 | B1 | 2/2015 | Guo et al. |

| | | | |
|---|---|---|---|
| 2005/0075361 | A1 | 4/2005 | Wang |
| 2010/0068786 | A1 | 3/2010 | Chmielewski et al. |
| 2011/0160239 | A1 | 6/2011 | Brodbeck et al. |
| 2011/0245287 | A1 | 10/2011 | Holaday et al. |
| 2015/0307505 | A1 | 10/2015 | Singh |

FOREIGN PATENT DOCUMENTS

| | | |
|---|---|---|
| EP | 1 422 230 A1 | 5/2004 |
| WO | 03/032990 A2 | 4/2003 |
| WO | 2004/103317 A2 | 12/2004 |
| WO | 2013/123824 A1 | 8/2013 |
| WO | 2015/168014 A1 | 11/2015 |
| WO | 2015/168031 A1 | 11/2015 |

OTHER PUBLICATIONS

International Search Report and Written Opinion corresponding to PCT/US2015/027820 mailed Jul. 3, 2015 (14 pages).
International Search Report and Written Opinion corresponding to PCT/US2015/027781 mailed Sep. 9, 2015 (19 pages).
Bagnol, D. et al., "Cellular Localization and Distribution of the Cloned Mu and Kappa Opioid Receptors in Rat Gastrointestinal Tract," *Neuroscience* (Nov. 1, 1997); 81(2):579-591.
Berge, Stephen M. et al., "Pharmaceutical Salts," *Journal of Pharmaceutical Sciences* (Jan. 1, 1977); 66(1): 1-19.
Bhounsule, Sushama A. et al., "Gastrointestinal actions of buprenorphine: are different receptors involved?" *European Journal of Pharmacology* (Dec. 1, 1996); 361(2-3):253-256.
Camilleri, M. "Current and future pharmacological treatments for diarrhea-predominant irritable bowel syndrome," *Expert Opinion on Pharmacotherapy* (Jun. 1, 2013); 14(9):1151-1160.
Feinberg, Andrew et al., "The opiate receptor: A model explaining structure-activity relationships of opiate agonists and antagonists," *Proc. Natl. Acad. Sci. USA* (Nov. 1, 1976); 73(11):4215-4219.
Haddad, Nizar et al., "Synthesis of a salbutamol dimer," *Tetrahedron Letters* (Feb. 11, 2002); 43(7):1135-1137.
Richards, Ryan, "Opioid Analgesics" (www.faculty.smu.edu): "A free phenol group is crucial for analgesic activity." (Oct. 29, 2015); 51 pages.
Rumack, Barry H., M.D. et al., "Acetaminophen Poisoning and Toxicity," *Pediatrics* (Jun. 1, 1975); 55:871-876.
Thorpe, David H., M.D., "Opiate Structure and Activity—A Guide to Understanding the Receptor," *Anesth Analg.* (Feb. 1, 1984); 63:143-151.
Zakko, S. et al., "Randomised clinical trial: the clinical effects of a novel neurokinin receptor antagonist, DNK333, in women with diarrhea-predominant irritable bowel syndrome," *Alimentary Pharmacology & Therapeutics* (Apr. 20, 2011); 33(12):1311-1321.

* cited by examiner

*Primary Examiner* — Charanjit Aulakh
(74) *Attorney, Agent, or Firm* — Mintz, Levin, Cohn, Ferris, Glovsky and Popeo, P.C.

(57) ABSTRACT

The present invention provides a buprenorphine dimer compound, wherein the two buprenorphine portions are linked via an ethylene spacer, wherein the spacer is bonded to the two opioid molecules via an ether bond. Pharmaceutical compositions comprising such a buprenorphine dimer drug are also disclosed, and the use of such compounds in the treatment of gastrointestinal hyperalgesia generally and in particular diarrhea-predominant irritable bowel syndrome.

9 Claims, 11 Drawing Sheets

Stability of the buprenorphine dimer when exposed to CYP enzymes in the presence and absence of a cofactor Stability of the buprenorphine dimer to aqueous conditions, as well as acidic and basic condition, each at room temperature and at 140°F for the indicated period of time.

Results of buprenorphine dimer receptor binding experiments – μ receptor

Results of buprenorphine dimer receptor binding experiments – κ receptor

µ agonist functional assay results for the buprenorphine dimer

μ antagonist functional assay results for the buprenorphine dimer

Results of oral and IV bioavailability of the buprenorphine dimer

Buprenorphine dimer decreases fecal output in a dose-dependent manner

Effect of the buprenorphine dimer on gastrointestinal motility in post inflammatory models

BUPRENORPHINE DIMER AND ITS USE IN TREATMENT OF GASTROINTESTINAL DISORDERS

CROSS-REFERENCES TO RELATED APPLICATIONS

This application claims the benefit of priority under 35 U.S.C. §119(e) to U.S. Provisional Application Ser. No. 61/985,207, filed Apr. 28, 2014; U.S. Provisional Application Ser. No. 62/101,768, filed Jan. 9, 2015; and U.S. Provisional Application Ser. No. 62/176,883, filed Jan. 9, 2015; the disclosures of each being incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Buprenorphine

Buprenorphine is a semi-synthetic, mixed μ agonist-κ-antagonist opioid receptor modulator that is used to treat opioid addiction in higher dosages, to control moderate acute pain in non-opioid-tolerant individuals in lower dosages and to control moderate chronic pain in even smaller doses. Its structure is:

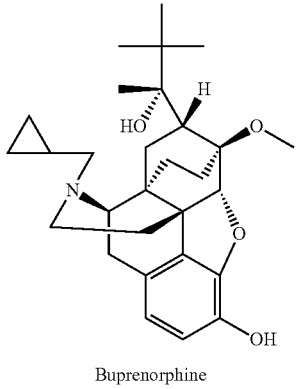 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

Buprenorphine

Buprenorphine is currently indicated for the treatment of pain as intravenous, sublingual and transdermal dosage forms. Buprenorphine is also indicated for the treatment of opiate addiction. Although buprenorphine has a long half-life and can be administered once daily, the oral bioavailability of buprenorphine is very low due to extensive presystemic extraction. Consequently sublingual administration of buprenorphine is required to achieve clinically effective systemic plasma concentrations. Even with sublingual administration, buprenorphine is only about 30% available to systemic circulation.

Diarrhea-Predominant Irritable Bowel Syndrome

Diarrhea-predominant irritable bowel syndrome (IBS-D) is a highly prevalent gastrointestinal disorder that is often accompanied, in addition to diarrhea, by both visceral and somatic hyperalgesia (enhanced pain from colorectal and somatic stimuli), discomfort, bloating, and gas.

According to the International Foundation for Functional Gastrointestinal Disorders, IBS-D is estimated to affect between 25-45 million Americans. It is the most common diagnosis made by gastroenterologists, and is one of the disorders most frequently treated by primary care physicians.

Irritable bowel syndrome has a very heavy impact on the quality of life and has high social costs. The disease has a fluctuating trend, but tends to be chronic or subchronic. Although there is no evidence that the presence of IBS involves deterioration in patient life expectancy, it significantly reduces health-related quality of life and work productivity. In the more severe cases patients may experience several episodes of abdominal pain and diarrhea per day resulting in severe impairment of relationships and in the workplace.

IBS-D Treatments

Bile acid binders, amitryptyline, probiotics, mast cell stabilizers and 5-ASA have been used off-label in the treatment of IBS-D, albeit without compelling evidence of chronic efficacy. The anti-diarrheal loperamide, a synthetic opioid, has been used similarly, but its uninhibited full μ opioid agonist activity often results in severe constipation.

Among drugs in development for IBS-D is LX 1033, an inhibitor of serotonin synthesis in the gastro-intestinal tract, currently being developed by Lexicon Pharmaceuticals. Its mechanism of action, however, does not support pain alleviation. DNK-333 (Novartis), a neurokinin antagonist, was withdrawn from study for IBS-D following Phase II studies for want of efficacy. Ibodutant (Menarini), another neurokinin antagonist in Phase II trials, showed no efficacy over placebo in the overall population, and is being pursued in further testing only in women. Rifaximin (Salix Pharmaceuticals) has been studied for IBS-D, showing moderate activity, but there is significant concern for the development of antibiotic resistance and continued efficacy.

Latronex (alosetron, Prometheus Laboratories, Inc.) is the only drug approved for IBS-D in the United States, albeit only for women. It has no demonstrated analgesic properties. Importantly, it has a black box warning for serious adverse effects including, specifically, ischemic colitis.

To date, no drug has been approved in the United States for chronic, unrestricted treatment of IBS-D.

Eluxadoline (Forest Laboratories, Inc.) is a μ opioid receptor agonist and δ opioid receptor antagonist that has met primary endpoints of improvement of stool consistency and reduction of abdominal pain in Phase III testing. Its effect on pain reduction is modest at best and without a demonstrable effect on reducing colonic hypersensitivity that results in hyperalgesia. Moreover, several cases of pancreatitis, a potentially life threatening disease, were reported in Phase II trials. Cases of pancreatitis were reported even after patients with a known history of biliary disease were excluded from clinical study enrollment. In general, μ agonists have a constricting effect on the Sphincter of Oddi, a muscular valve that regulates the flow of bile and pancreatic juice from the bile duct into the duodenum. Buprenorphine, because of its partial μ agonist effect and κ antagonist effect, does not result in increased tone or constriction of the Sphincter of Oddi. We expect that the buprenorphine dimer, with the same receptor pharmacology as buprenorphine, will also have no constricting effect on the Sphincter of Oddi.

There has accordingly been a long-standing need for a chronic treatment of IBS-D that decreases intestinal motility, thereby decreasing the incidence of diarrhea, is an analgesic, is not associated with pancreatitis, and more than merely treating symptoms, potentially addresses underlying hypersensitivity and resulting hyperalgesia associated with IBS-D.

BRIEF SUMMARY OF THE INVENTION

In one aspect, provided herein is a novel dimer comprising two buprenorphine drug molecules, conjugated to each other by O-alkylation through their phenolic groups to yield the structure of Formula (I):

Formula (I)

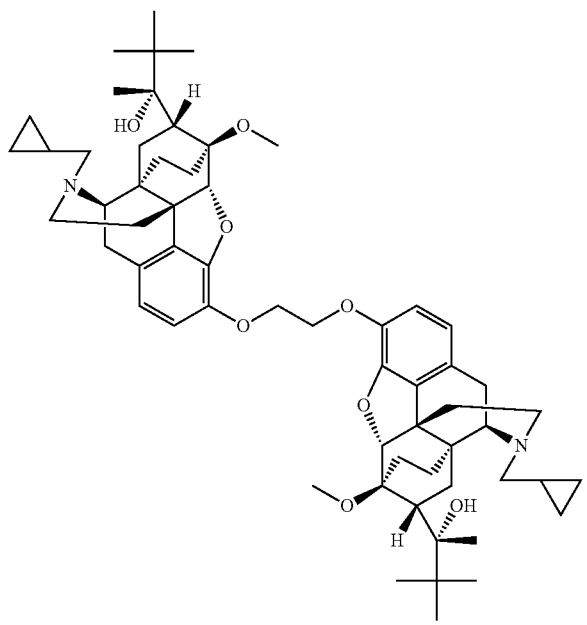

or a pharmaceutically acceptable salt or solvate thereof

In Formula (I), the compound is: 2,2'-((4aR,4a'R,6S,6'S,7S,7'S,12bR,12b'R)-9,9'-(ethane-1,2-diylbis(oxy))bis(3-(cyclopropylmethyl)-7-methoxy-1,2,3,4,5,6,7,7a-octahydro-4a,7-ethano-4,12-methanobenzofuro[3,2-e]isoquinoline-9,6-diyl))bis(3,3-dimethylbutan-2-ol) (Compound 1, or buprenorphine dimer). Its molecular weight is 961.28.

Initially, we synthesized this buprenorphine dimer intending to achieve a prodrug that would deter abuse. By dimerizing the parent compounds at their phenolic hydrogen positions, we believed opioid activity would be abated pending first-pass metabolism in the liver to release the parent compound. We believed that drug metabolism would be facilitated by cytochrome P-450 enzymes (CYP 3A4 and CYP2D6) when they interacted with the methylene carbons attached to the phenolic oxygen molecules of the dimer. The resulting O-dealkylation would eventually release buprenorphine into systemic circulation.

Our expectations were supported by the literature regarding conjugation to phenolic hydrogen generally, albeit not with our particular linker. Conventional wisdom has been that derivatization of the phenolic groups of morphinones by replacing hydrogen with a less hydrophilic substituent would substantially reduce the opioid potency of the resulting opioid. See Feinberg Andrew F, et al. *Proc Natl Acad Sci. USA* Volume 73 no 11 p 4215-4219 (1976). According to R. Richards, *Opioid Analgesics* (www.faculty.smu.edu): "A free phenol group is crucial for analgesic activity." In *Anesth Analg* 1984; 63; 143-51 at 145 et seq, D. H. Thorpe says "Another portion of the morphine molecule thought to interact with the receptor is the phenol moiety. Muzzling the free hydroxyl group with a methyl group reduces potency more than tenfold . . . . " The author goes on to cite other studies showing that larger alkyl groups have an even more deleterious effect, concluding that "bulkiness . . . is responsible for the decreased binding effect." See also U.S. Pat. Nos. 8,183,376 and 8,461,171.

Despite these expectations, the resulting dimer turned out to have wholly unanticipated properties, unsuiting its utility as a prodrug but suiting it for very different indications than those we first envisioned. The buprenorphine moieties, far from exhibiting the steric hindrance we anticipated, retained their characteristic opiate receptor pharmacology. The dimer proved resistant to enzymatic metabolism in the gastrointestinal milieu. It is also highly resistant to tampering, as by free-basing. When orally administered it is essentially non-absorbed and so does not enter the systemic circulation. These serendipitous observations led us to conceive new indications that were advantaged by these properties, viz, peripheral analgesia in the GI tract.

The novel compound of the invention addresses a long-felt need for an effective treatment of IBS-D that addresses both pain and diarrhea, reduces visceral (colonic) hypersensitivity, does not have the drawbacks of other agents utilized for this purpose and that can be prescribed safely on a chronic basis. Accordingly, the invention comprises the use of the compound for the treatment of IBS-D, especially when visceral hypersensitivity and hyperalgesia are present. The compound may also find application as an adjuvant with other drugs such as teduglutide for treating other intestinal conditions such as short bowel syndrome, to safely reduce intestinal transit time. Pharmaceutical compositions according to the invention comprise a buprenorphine dimer of Formula (I) formulated as an oral tablet or capsule, extended release oral tablet or capsule, intramuscular or subcutaneous depot injection, or transdermal patch.

DETAILED DESCRIPTION OF THE INVENTION

Figure 1:
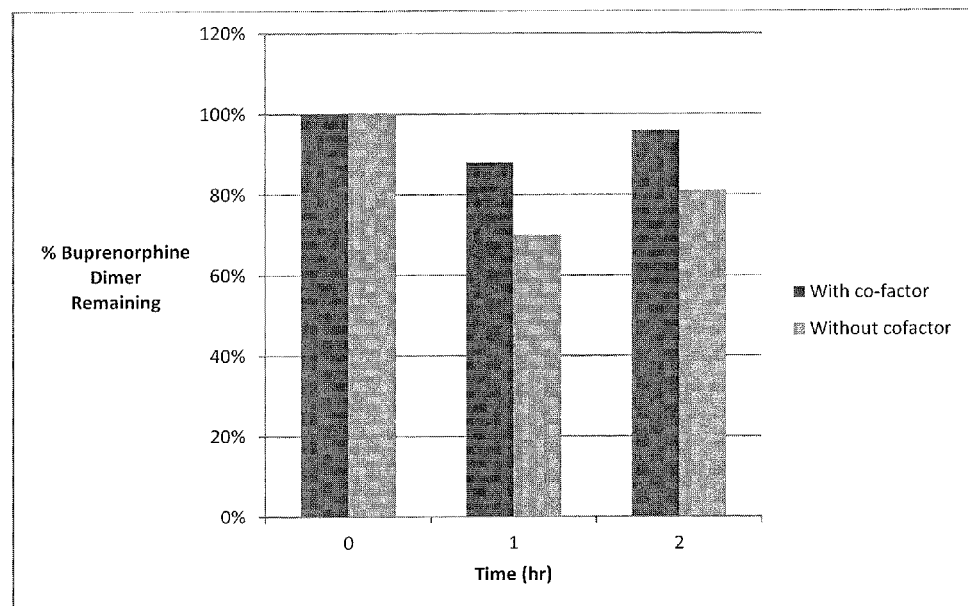
FIG. 1 provides a bar chart illustrating the stability of buprenorphine dimer when exposed to CYP enzymes in the presence and absence of a co-factor.

The buprenorphine dimer of the invention exhibits the $\mu$-receptor partial agonist and full $\kappa$-receptor antagonist activity characteristic of the parent buprenorphine. The $\kappa$-receptor antagonist activity is very important since it appears to have multiple functions. As the receptor agonist dimer described herein also has a $\kappa$-receptor antagonist effect, the $\mu$-receptor agonist reduction of intestinal motility is moderated, reducing the possibility of significant constipation. In addition, $\kappa$-receptor antagonist effect appears to prevent the constrictive $\mu$-receptor agonist effect on the smooth muscle tissue of the Sphincter of Oddi, avoiding the possibility of pancreatitis. In animal and human studies, it has been shown that buprenorphine also reduced colonic and skin hypersensitivity and hyperalgesia. Visceral hypersensitivity is an important component of the etiology of IBS-D and we believe that κ-receptor antagonism of the buprenorphine dimer will play an important role in symptom reduction. We have now also further demonstrated in animal models that the described buprenorphine dimer, owing to its conjoint retention of buprenorphine receptor pharmacology and non-systemic absorption (i.e., no absorption from the intestinal tract), is suitable for the chronic treatment of IBS-D, while substantially eliminating the prospects for abuse. This surprising discovery indicates that the dimer described herein would be superior to available agents that are utilized in the treatment of IBS-D because it (1) addresses the underlying visceral (colonic) hypersensitivity and consequent hyperalgesia characteristic of IBS-D, (2) will side-step the possibility of pancreatitis associated with eluxadoline, (3) will mitigate diarrhea without the risk of constipation; and (4) will achieve the foregoing without the troublesome systemic and central nervous system adverse effects attributed to buprenorphine itself.

As noted above, the present invention provides a dimeric form of buprenorphine where the two buprenorphine molecules are linked via a covalent bond between the phenolic (3-hydroxyl) functional group of each buprenorphine molecule and an ethylene linker. The ethylene linker serves as a spacer between the two buprenorphine molecules and is thought to prevent the two bulky buprenorphine molecules from adopting an enclosed ring conformation via either a covalent, ionic or Van der Waal interaction between other functional groups on the molecules.

Surprisingly, when two drug molecules are conjugated to each other via an ethylene spacer, wherein the spacer is attached to the phenyl ring of each drug molecule via an ether bond, the resulting dimer is found to be chemically and metabolically stable, and is not de-conjugated when exposed to metabolic enzymes. Additionally, surprisingly and unexpectedly, the dimer retains the pharmacological activity of the parent compound, yet has negligible systemic exposure upon oral administration.

In contrast to buprenorphine, the buprenorphine dimer, prepared as described herein, is found to be not absorbed after oral administration and furthermore retains the opioid μ and κ activity not only in form but also direction, viz. neither receptor affinity nor activity is compromised. Additionally, the buprenorphine dimer described herein is relatively stable to metabolism in in vivo and in vitro experiments. The buprenorphine dimer appears metabolically stable, even after exposure to the liver of live mice, following intravenous injection. Thus, surprisingly and unexpectedly, despite the loss of absorptive properties as manifested by lack of gastrointestinal absorption and metabolic inactivation, the opioid functionality of the dimer was not lost and its gastrointestinal opioid effects were manifested as a decrease of motility and anti-diarrheal response after oral dosing. The gastrointestinal effects were proportional to dose in mice models where diarrhea (increased excreted pellets) is produced by a combination of physical and psychological stress. In another mouse model experiment in which the colon was sensitized by an inflammatory insult, the favorable response persisted beyond the acute period, three weeks after the acute insult, possibly indicating an effect of the dimer on decreasing the hypersensitivity and hyperalgesia of the mouse colonic membranes.

Still further, it was also found that the buprenorphine dimer retained, selectively, only the μ and the κ functions of buprenorphine, but was significantly stripped of its δ function. Stated differently, the buprenorphine dimer, unlike buprenorphine, is a selective μ and κ active molecule without significant δ activity.

Synthesis of the Buprenorphine Dimer

Synthesis of the buprenorphine dimer provided herein can proceed by a general O-alkylation reaction in an organic solvent (such as, e.g., acetonitrile, DMF, DMSO, NMP, DCM, THF, 1,4-Dioxane) in the presence of inorganic base (such as, e.g., sodium hydroxide, potassium carbonate, sodium carbonate, cesium carbonate, potassium bicarbonate and sodium bicarbonate) or organic base (such as, e.g., triethylamine, Hunig's base, DMAP and pyridine) at room temperature or elevated temperature. Suitable alkylating agents that can be used include diiodo, dibromo, dichloro, ditosylate, dimesylate and ditriflate reagents (e.g., 1,2-ethylene ditosylate, 1,2-ethylene dimesylate). The free base or a salt of buprenorphine can be employed as a starting material in the synthesis.

Pharmaceutical Compositions of the Dimer—General

In certain embodiments, provided herein are compositions comprising a buprenorphine dimer of Formula (I). A pharmaceutical composition can further comprise a pharmaceutically acceptable carrier. Illustrative pharmaceutically acceptable carriers and formulations are described below. Such pharmaceutical compositions can be used to treat diarrhea-predominant IBS.

As will be appreciated, a pharmaceutically acceptable salt of a dimer may be used instead of or in addition to a dimer in any or all of the compositions and methods of treating discussed herein. Thus, in specific embodiments, a pharmaceutically acceptable salt of the dimer (i.e., any pharmaceutically acceptable salt of any of the dimers) is used in the methods of the invention. These salts can be prepared, for example, in situ during the final isolation and purification of the compound or by separately reacting the purified compound in its free base form with a suitable organic or inorganic acid and isolating the salt thus formed. In some embodiments, the pharmaceutically acceptable salt of the buprenorphine dimer is prepared using acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid. For further description of pharmaceutically acceptable salts that can be used in the methods described herein see, for example, S. M. Berge et al., "Pharmaceutical Salts," 1977, *J. Pharm. Sci.* 66:1-19, which is incorporated herein by reference in its entirety.

The buprenorphine dimer of the invention can exist in unsolvated as well as solvated forms with pharmaceutically acceptable solvents such as water, ethanol, and the like. In general, the solvated forms are considered equivalent to the unsolvated forms for the purposes of the present invention. In a specific embodiment, the solvated form of the dimer is a hydrate.

In general, salt formation may improve shelf life of the resultant therapeutic agent. Appropriate salt synthesis can afford products that are crystalline, less prone to oxidation and easy to handle. Various salts can be prepared that would afford stable and crystalline compounds. A few examples are hydrochloric, sulfuric, p-toluenesulfonic, methanesulfonic, malonic, fumaric, and ascorbic acid salts.

In certain specific embodiments, such a pharmaceutical composition is formulated as oral tablet or capsule, extended release oral tablet or capsule (hard gelatin capsule, soft gelatin capsule), sublingual tablet or film, or extended release sublingual tablet or film. Illustrative pharmaceutically acceptable carriers and formulations are described in more detail below.

Methods of Treatment—General

In specific embodiments, provided herein is a method for the treatment of Diarrhea-Predominant Irritable Bowel Syndrome by reducing diarrhea, pain and gut hypersensitivity and hyperalgesia in a patient comprising oral administration of a therapeutically effective amount of the dimer. A therapeutically effective amount is an amount which yields an appreciable and beneficial effect in a statistically significant number of patients. In certain embodiments, the patient is a mammal. In more specific embodiments, the patient is a human. In certain specific embodiments, the patient is a domesticated mammal such as a dog, a cat, or a horse.

Pharmaceutical Compositions, Dosing and Routes of Administration

The IBS-D drug provided herein can be administered to a subject orally in the conventional form of preparations, such as capsules, microcapsules, tablets, granules, powder, troches, pills, suppositories, oral suspensions, syrups, oral gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrrolidone or aluminum stearate), a dispersing agent (e.g., hydroxypropylmethylcellulose), a diluent (e.g., water), and base wax (e.g., cocoa butter, white petrolatum or polyethylene glycol).

The dose of the buprenorphine dimer provided herein to be administered to a patient is rather widely variable and can be subject to the judgment of a health-care practitioner. Dosage may be properly varied depending on the age, body weight and medical condition of the subject and the type of administration. In one embodiment, one dose is given per day. In any given case, the amount of the dimer provided herein administered will depend on such factors as the solubility of the active component, the formulation used and the route of administration. The effective amount of the buprenorphine dimer drug provided herein in the pharmaceutical composition will be at a level that will exercise the desired effect, preferably, for example, about 0.15 mg/kg of an IBS-D patient's body weight to about 7.2 mg/kg of a patient's body weight, more preferably from about 0.7 mg/kg of an IBS-D patient's body weight to about 3.0 mg/kg of a patient's body weight, and still more preferably about 1.5 mg/kg of a patient's body weight in unit dosage for oral administration. Alternatively, from about 10 to about 500 mg, preferably from about 50 to about 200 mg, more preferably about 100 mg, will be administered to an IBS-D patient.

The buprenorphine dimer provided herein can be administered, e.g., once, twice, or three times daily, preferably once per day. The dimer provided herein can be administered orally for reasons of convenience. In one embodiment, when administered orally, the dimer provided herein is administered with a meal and water. In another embodiment, the dimer provided herein is dispersed in water or juice (e.g., apple juice or orange juice) and administered orally as a suspension.

Alternatively, the buprenorphine dimer provided herein can also be administered rectally or by other transmucosal routes. The mode of administration is left to the discretion of the health-care practitioner.

In one embodiment, provided herein are capsules containing the dimer without an additional carrier, excipient or vehicle.

In another embodiment, provided herein are compositions comprising an effective amount of the dimer and a pharmaceutically acceptable carrier or vehicle, wherein a pharmaceutically acceptable carrier or vehicle can comprise an excipient, diluent, or a mixture thereof.

The oral compositions can be in the form of tablets, chewable tablets, capsules, solutions, troches and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a dimer provided herein with a suitable carrier or diluent and filling the proper amount of the mixture into capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer the drug provided herein as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the drug provided herein can be delayed or prolonged by proper formulation. For example, a slowly soluble pellet of the dimer can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time.

EXAMPLES

The following examples are offered to illustrate, but not to limit the claimed invention.

Example 1
Synthesis
Buprenorphine dimer was synthesized as shown below.
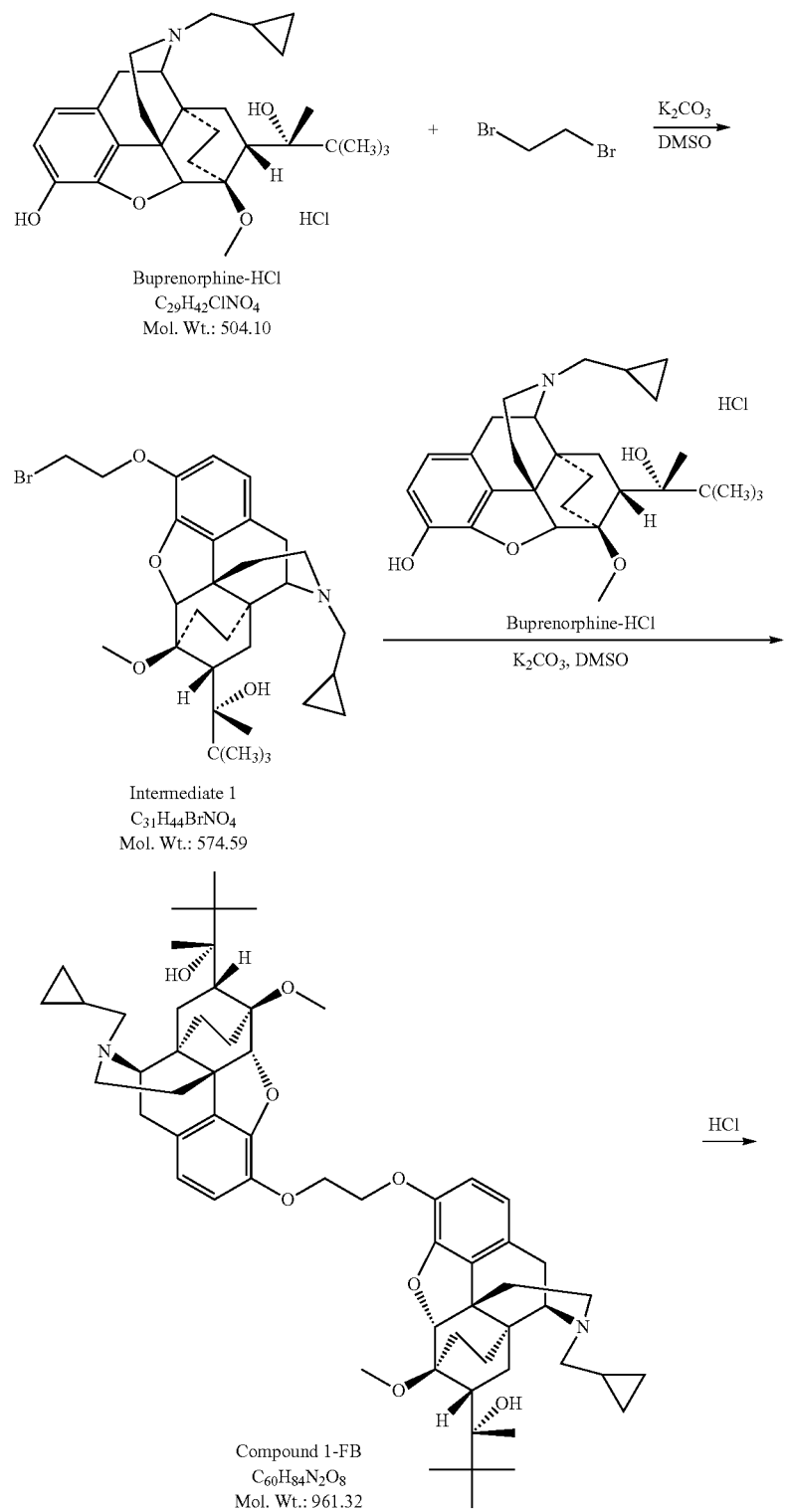

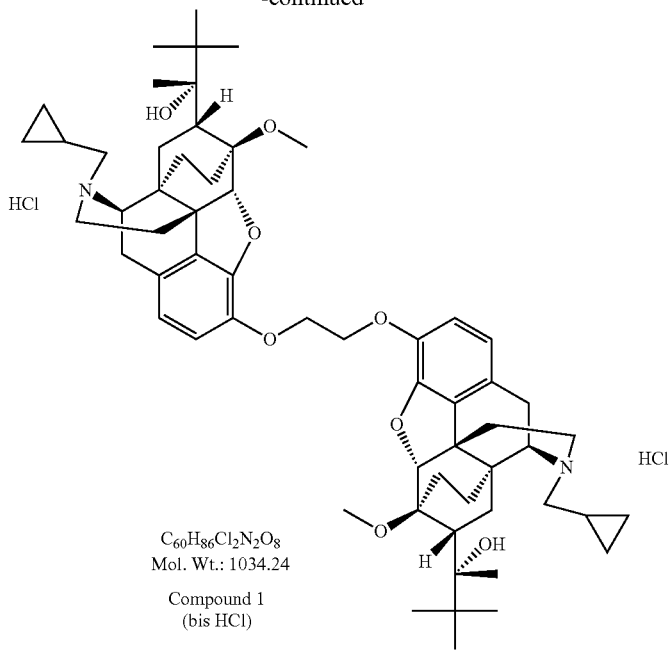

C<sub>60</sub>H<sub>86</sub>Cl<sub>2</sub>N<sub>2</sub>O<sub>8</sub>
Mol. Wt.: 1034.24
Compound 1
(bis HCl)

Buprenorphine HCl-salt (5.0 g, 10.68 mmol, 1 equiv) and potassium carbonate (42.73 mmol, 4 equiv) were charged in a 3-neck round bottom flask followed by anhydrous DMSO (50 ml, 10 vol). The mixture was heated to 60° C. and 1,2-dibromoethane (9.2 mL, 106.8 mmol, 10 equiv) was added slowly. The reaction mixture was stirred at 60° C. for 16 h then cooled to room temperature, diluted with water and extracted with dichloromethane. The combined organic portions were washed with brine, dried (anhydrous $Na_2SO_4$), filtered and concentrated under reduced pressure to afford a viscous liquid. The crude product was purified by silica gel chromatography using 0-5% MeOH/DCM to afford 4.2 g (69%) Intermediate 1 as off-white foamy solid.

Buprenorphine HCl-salt (1.74 g, 3.72 mmol) and potassium carbonate (2.0 g, 14.87 mmol, 4 equiv) were charged in a 3-neck round bottom flask followed by anhydrous DMSO (10 mL). The mixture was heated to 60° C. and Intermediate 1 (3 g, 5.22 mmol, 1.4 equiv) dissolved in 7 mL of anhydrous DMSO was added dropwise over a period of 2 h. The reaction mixture was stirred at 60° C. for 16 h then cooled to room temperature, diluted with water and extracted with dichloromethane. The organic layer was washed with brine, dried (anh. $Na_2SO_4$), filtered and concentrated under reduced pressure to afford a viscous liquid. The crude product was purified by silica gel chromatography using 0-5% MeOH/DCM to afford Buprenorphine dimer-FB (free base) as foamy solid (2.8 g, 77%).

5.5 g (5.7 mmol) of bi-conjugate (buprenorphine dimer-FB) was dissolved in 50 mL of ethyl acetate at room temperature under nitrogen. 3.43 mL (6.9 mmol, 1.2 equiv) of 2N HCl in ether was added drop-wise at room temperature. The reaction mixture was stirred at room temperature for additional hour and filtered to obtain a solid. The solid was further washed with 100 ml of ethyl acetate and dried under vacuum to afford buprenorphine dimer (bis HCl salt) as white solid (5.8 g, 98%). $^1$H NMR (300 MHz, DMSO-$d_6$): δ 9.75 (br, 2H), 6.88 (d, J=9.2 Hz, 2H), 6.67 (d, J=9.2 Hz, 2H), 4.66 (s, 2H), 4.23-4.42 (m, 4H), 3.84-3.92 (m, 2H), 3.40 (s, 6H), 3.21-3.35 (m, 5H), 2.98-3.20 (m, 7H), 2.64-2.85 (m, 4H), 2.12-2.26 (m, 4H), 1.72-1.94 (m, 4H), 1.38-1.52 (m, 4H), 1.26 (s, 6H), 0.99 (s, 20H), 0.48-0.76 (m, 10H), 0.32-0.42 (m, 4H); MS: m/z 962 (M+1)$^+$ Example 2

Illustrative Pharmaceutical Compositions

The following composition can be used for an oral tablet of Buprenorphine dimer.

TABLE 1

| Ingredients | % w/w |
| --- | --- |
| Dimer | 2 |
| Lactose | 83.6 |
| Colloidal Silicon dioxide | 0.67 |
| Microcrystalline cellulose | 10 |
| Croscarmellose sodium | 3.4 |
| Magnesium stearate | 0.33 |

Example 3

Assays

In Vitro Assay: Metabolic Stability of Buprenorphine Dimer

Incubations of the dimer (e.g., 1 μM) with human liver microsomes (e.g., 1 mg protein/mL) was carried out using a Tecan Liquid Handling System (Tecan), or equivalent, at 37±1° C. in 0.2-mL incubation mixtures (final volume) containing potassium phosphate buffer (50 mM, pH 7.4), MgCl$_2$ (3 mM) and EDTA (1 mM, pH 7.4) with and without a cofactor, NADPH-generating system, at the final concentrations indicated in a 96-well plate format. The NADPH-generating system consisted of NADP (1 mM, pH 7.4), glucose-6-phosphate (5 mM, pH 7.4) and glucose-6-phosphate dehydrogenase (1 Unit/mL). The dimer was dissolved in aqueous methanolic solution (methanol 0.5% v/v, or less). Reactions were started typically by addition of the cofactor, and stopped at four designated time points (e.g., up to 120 min) by the addition of an equal volume of stop reagent (e.g., acetonitrile, 0.2 mL containing an internal standard). Zero-time incubations served as 100% value to determine percent loss of substrate. Incubations were carried out in triplicate with an exception for zero-time samples (which were incubated in quadruplicate). Zero-cofactor (no NADPH) incubations were performed at zero-time and the longest time point. The samples were subjected to centrifugation (e.g., 920×g for 10 min at 10° C.) and the supernatant fractions analyzed by LC-MS/MS. Additional incubations were carried out with microsomes in which were replaced with a marker substrate (e.g., dextromethorphan to monitor substrate loss) as positive controls to determine if the test system is metabolically competent.

The above samples were analyzed by LC-MS/MS. Analysis was performed for the samples at each incubation solution. Results were determined by a comparison of peak ratios over the time course of the experiment (typically reported as "% Parent Remaining").

Data were calculated with a LIMS (includes Galileo, Thermo Fisher Scientific Inc. and reporting tool, Crystal Reports, SAP), the spreadsheet computer program Microsoft Excel (Microsoft Corp.) or equivalent. The amount of unchanged parent compound will be estimated (to determine approximate percent substrate remaining in each incubation) based on analyte/internal standard (IS) peak-area ratios using a LIMS, Analyst Instrument Control and Data Processing Software (AB SCIEX), or equivalent.

Results: Results as shown in FIG. 1 indicate that the dimer of buprenorphine was relatively stable in presence of microsomal enzymes for the duration of the assay. The microsomal enzymes are typically responsible for metabolism of drugs such as buprenorphine. The dimer was stable in presence of the microsomes, with or without the co-factor. The assay was terminated at 2 hours as enzymes are typically not stable beyond 2 hours at incubation temperatures of 37° C.

Stability Assay

The goal of the laboratory-based studies was to evaluate the ease with which the patient can retrieve buprenorphine from the dimer and thus compromise its abuse deterrent properties.

These studies facilitate the understanding of the ease with which a potential abuser could cleave the dimer using household chemicals such as baking soda, acid or simple heating in water. Buprenorphine dimer stability was assessed at room temperature in untreated tap water and in presence of acid (1N HCl) or base (5% aqueous sodium bicarbonate). The dimer was relatively stable under those conditions and under these conditions did not appreciably degrade to buprenorphine. See FIG. 2.

Figure 2:
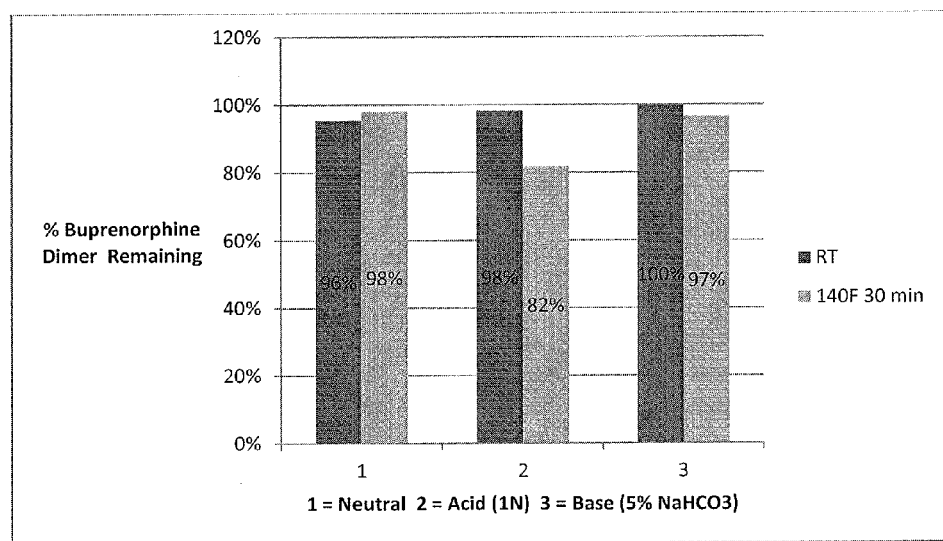
FIG. 2 provides a bar graph showing the stability of buprenorphine dimer to aqueous conditions, as well as acidic and basic condition, each at room temperature and at 140° F. for the indicated period of time.

Results: As shown in FIG. 2, the buprenorphine dimer remained stable and did not degrade to release buprenorphine either at room temperature or elevated temperature under extreme pH conditions even as long as 30 minutes.

These studies also facilitate the understanding of the stability of the dimer in the gastrointestinal tract, which exhibits a gradient pH along its length in both IBS-D and healthy patients. The pH ranges from 1 due to excretion of hydrochloric acid from the parietal cells of the stomach to 8 in the colon. The proximal portion of the gastrointestinal tract is most acidic where the distal end is the least acidic.

Example 4

Receptor Binding Activity

This example illustrates the binding of the buprenorphine dimer provided herein to the following receptors: µ-opioid receptor; κ-opioid receptor; and δ-opioid receptor.

Human µ Opioid Receptor Binding Assay

Figure 3:
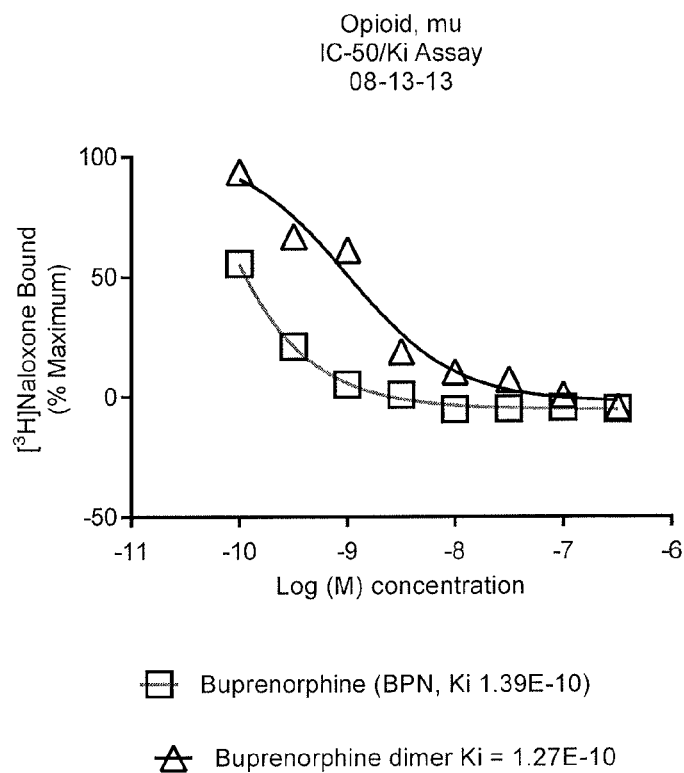
FIG. 3 provides the results of buprenorphine dimer receptor binding experiments—$\mu$ receptor.

Membranes from Chinese Hamster Ovary cells expressing the human µ opioid receptor (Perkin Elmer #RBHOMM400UA) were homogenized in assay buffer (50 mM Tris, pH 7.5 with 5 mM MgCl2) using glass tissue grinder, Teflon pestle and Steadfast Stirrer (Fisher Scientific). The concentrates of the membranes were adjusted to 300 µg/mL in assay plate, a 96 well round bottom polypropylene plate. The compound to be tested was solubilized in DMSO (Pierce), 10 mM, then diluted in assay buffer to 3.6 nM. In a second 96 well round bottom polypropylene plate, known as the premix plate, 60 µL of 6× compound was combined with 60 µL of 3.6 nM $^3$H-Nalaxone. From the premix plate 50 µL was transferred to an assay plate containing the membranes, in duplicate. The assay plate was incubated for 2 h at room temperature. A GF/C 96 well filter plate (Perkin Elmer #6005174) was pretreated with 0.3% polyethylenimine for 30 min. The contents of the assay plate were filtered through the filter plate using a Packard Filtermate Harvester, and washed 3 times with 0.9% saline at 4° C. The filter plate was dried, underside sealed, and 304, Microscint 20 (Packard #6013621) was added to each well. A Topcount-NXT Microplate Scintillation Counter (Packard) was used to measure emitted energies in the range of 2.9 to 35 KeV. Results were compared to maximum binding, wells receiving no inhibitions. Nonspecific binding was determined in presence of 50 µM unlabeled naloxone. The biological activity of the dimer is shown in FIG. 3.

Results: The graphs in FIG. 3 show that the dimer has significant affinity for the opioid µ receptor The opioid µ receptor affinity of the buprenorphine dimer at $10^{-8}$M (~10 ng) and the profile was similar to that of buprenorphine.

Human κ Opioid Receptor Binding Assay

Figure 4:
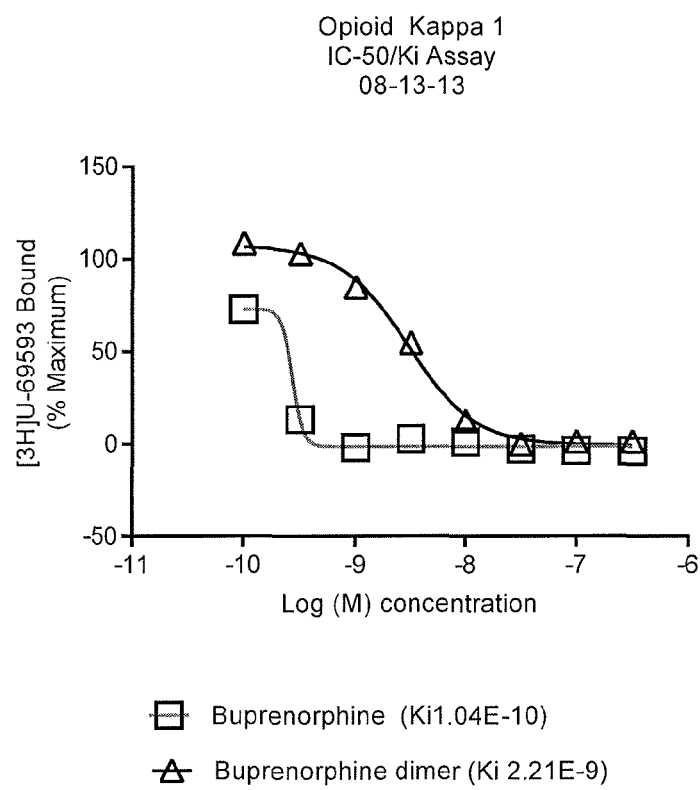
FIG. 4 provides the results of buprenorphine dimer receptor binding experiments—$\kappa$ receptor.

Membranes from cloned HEK-293 cells expressing the human kappa opioid receptor (Amersham Biosciences UK Ltd. 6110558 200U) were homogenized in assay buffer (50 mM Tris, pH 7.5 with 5 mM MgCl2) using glass tissue grinder, Teflon pestle and Steadfast Stirrer (Fisher Scientific). The concentrates of the membranes were adjusted to 300 µg/mL in assay plate, a 96 well round bottom polypropylene plate. The compound to be tested was solubilized in DMSO (Pierce), 10 mM, then diluted in assay buffer to 3.6 nM. In a second 96 well round bottom polypropylene plate, known as the premix plate, 60 µL of 6× compound was combined with 60 µL of 3.6 nM $^3$H-Diprenorphine (DPN). From the premix plate, 50 µL was transferred to an assay plate containing the membranes, in duplicate. The assay plate was incubated for 18 h at room temperature. A GF/C 96 well filter plate (Perkin Elmer #6005174) was pretreated with 0.3% polyethylenimine for 30 min. The contents of the assay plate were filtered through the filter plate using a Packard Filtermate Harvester, and washed 3 times with 0.9% saline at 4° C. The filter plate was dried, underside sealed, and 30 µL Microscint 20 (Packard #6013621) was added to each well. A Topcount-NXT Microplate Scintillation Counter (Packard) was used to measure emitted energies in the range of 2.9 to 35 KeV. Results were compared to maximum binding, wells receiving no inhibitions. Nonspecific binding was determined in presence of 50 µM unlabeled naloxone. The biological activity of the dimer is shown in FIG. 4.

Results: FIG. 4 describes the opioid κ receptor agonist profile of the buprenorphine monomer and the dimer. Neither the monomer nor the dimer of buprenorphine has lost its affinity for the κ receptor. Qualitatively, as with buprenorphine, the binding of the buprenorphine dimer to opioid κ receptor increases with concentration. It is estimated that at about 1 µg, the profile of the opioid κ receptor affinity of the dimer was similar to that of buprenorphine.

Human δ Opioid Receptor Binding Assay

The assay was designed to test the ability of a compound to interfere with the binding of tritiated naltrindole to the human δ subtype 2 opioid receptor. Membranes from Chinese Hamster Ovary cells expressing the human δ subtype 2 opioid receptor (Perkin Elmer #RBHODM400UA) were homogenized in assay buffer (50 mM Tris, pH 7.5 with 5 mM $MgCl_2$) using a glass tissue grinder, Teflon pestle and Steadfast Stirrer (Fisher Scientific). The concentration of membranes was adjusted to 100 µg/mL in an assay plate, a 96 well round bottom polypropylene plate. The compound to be tested was solubilized in DMSO, 10 mM, then diluted in assay buffer to 6× the desired final concentration. The ligand, $^3$H-natrindole (Perkin Elmer #NET-1065) was also diluted in assay buffer to 6 nM. Aliquots of $^3$H-natrindole (50 µL) were transferred to the assay plate containing the membranes in duplicate. The assay plate was incubated for 30 minutes at room temperature. A GF/C 96 well filter plate (Perkin Elmer #6005174) was pretreated with 0.3% polyethylenimine for 30 min. The contents of the assay plate were filtered through the filter plate using a Packard Filtermate Harvester, and washed 3 times with 0.9% saline at 4° C. The filter plate was dried, the underside sealed, and a 30 µL MictoS=scint 20 (Packard #6013621) added to each well. A Topcount-NXT Microplate Scintillation Counter (Packard) was used to measure emitted energies in the range of 2.9 to 35 KeV. Results were compared to maximum binding, wells receiving no inhibitors. Nonspecific binding was determined in the presence of 1 µM unlabelled Natrindole. The biological activity of the buprenorphine dimer is shown in Table 2 below.

TABLE 2

| Compound | IC50 | Ki |
| --- | --- | --- |
| Buprenorphine dimer | 7.6 nM | 2.87 nM |

Relative to the µ and κ opioid receptors, the dimer had poor affinity for the δ receptor.

Example 5

Receptor Stimulation Activity

This example illustrates the ability of the buprenorphine dimer compound provided herein to stimulate the µ-opioid receptor-mediated signaling.

µ Opioid Receptor Agonist and Antagonist Functional Assays: [$^{35}$S]GTPγS Binding Assay in Chinese Hamster Ovaries Expressing Human µ Receptors (CHO-hMOR) Cell Membranes Briefly, CHO-hMOR cell membranes were purchased from Receptor Biology Inc. (Baltimore Md.). About 10 mg/ml of membrane protein was suspended in 10 mM TRIS-HCl pH 7.2, 2 mM EDTA, 10% sucrose, and the suspension kept on ice. One mL of membranes was added to 15 mL cold binding assay buffer containing 50 mM HEPES, pH 7.6, 5 mM $MgCl_2$, 100 mM NaCl, 1 mM DTT and 1 mM EDTA. The membrane suspension was homogenized with a polytron and centrifuged at 3000 rpm for 10 min. The supernatant was done centrifuged at 18,000 rpm for 20 min. The pellet was resuspended in 10 ml assay buffer with a polytron.

The membranes were pre-incubated with wheat germ agglutinin coated SPA beads (Amersham) at 25° C., for 45 min in the assay buffer. The SPA bead (5 mg/ml) coupled with membranes (10 µg/ml) were then incubated with 0.5 nM [$^{35}$S]GTPγS in the assay buffer. The basal binding was that taking place in the absence of added test compound; this unmodulated binding was considered as 100%, with agonist stimulated binding rising to levels significantly above this value. A range of concentrations of receptor agonist SNC80 was used to stimulate [$^{35}$S]GTPγS binding. Both basal and non-specific binding were tested in the absence of agonist; non-specific binding determination included 10 µM unlabeled GTPγS.

Buprenorphine dimer was tested for function as an antagonist by evaluating its potential to inhibit agonist-stimulated GTPγS binding using D-Phe-Cys-Tyr-D-Trp-Orn-Thr-Pen-Thr-NH2 (CTOP) as the standard. Radioactivity was quantified on a Packard Top Count. The following parameters were calculated:

% Stimulation=[(test compound cpm−non-specific cpm)/(basal cpm−non-specific cpm)]*100%

Inhibition=(% stimulation by 1 µM SNC80−% stimulation by 1 µM SNC80 in presence of test compound)*100/(% stimulation by 1 µM SNC80−100).

Figure 5:
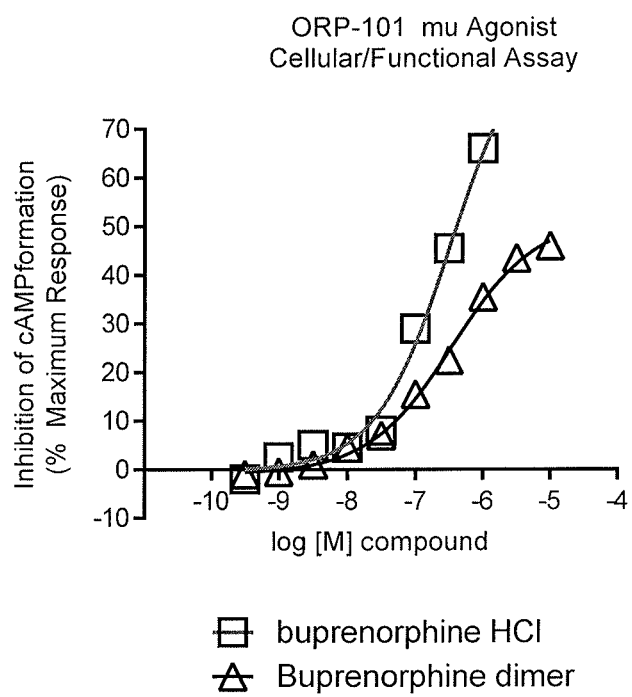
FIG. 5 provides $\mu$ agonist functional assay results for the buprenorphine dimer.
Figure 6:
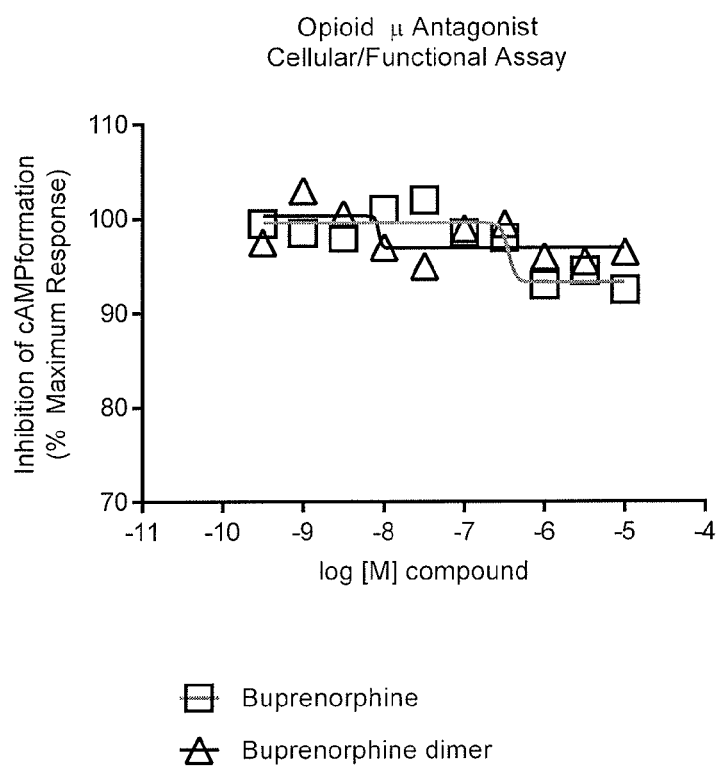
FIG. 6 provides $\mu$ antagonist functional assay results for the buprenorphine dimer.

$EC_{50}$ was calculated using GraphPad Prism. A graph for the compound tested is shown in FIGS. 5 and 6.

Results: Data shown in FIG. 5 indicates that the dimer is a potent µ agonist. The results also indicate that the opioid µ receptor activity of the dimer at $10^{-6}$M (~1 µg) is similar to that of buprenorphine. Data in FIG. 6 shows that the dimer does not function as a µ-antagonist.

Example 6

In Vivo Pharmacokinetic Study

The animal pharmacokinetic studies were conducted at John Hopkins Medical Institute. Animals used were CD-1 mice (about 35 gms, n=3 per time point). Drugs tested were buprenorphine and buprenorphine dimer. Dose 10 mg/kg IV and oral gavage. Blood collected at time 0, 30 min and 1, 2, 6 and 24 hours. Blood samples for the drug were analyzed after harvesting the plasma and by LC/MS/MS as follows:

A standard curve was prepared in mouse plasma spiked with the test drug (10-25000 nM). Plasma samples (50 µL) were extracted in 300 µL, acetonitrile containing losartan or buprenorphine-$d_4$ as internal standard. Extracts were centrifuged at 16000×g at 4° C. for 5 minutes. Supernatants (250 µL) were transferred to a new tube and dried under $N_2$ at 45° C. for 1 hour. Samples were reconstituted with 100 µL of 30% acetonitrile, vortexed and centrifuged. Supernatants (90 µL) were transferred to LC vials and 10 µL was injected on LC/MS. See FIG. 7.

Figure 7:
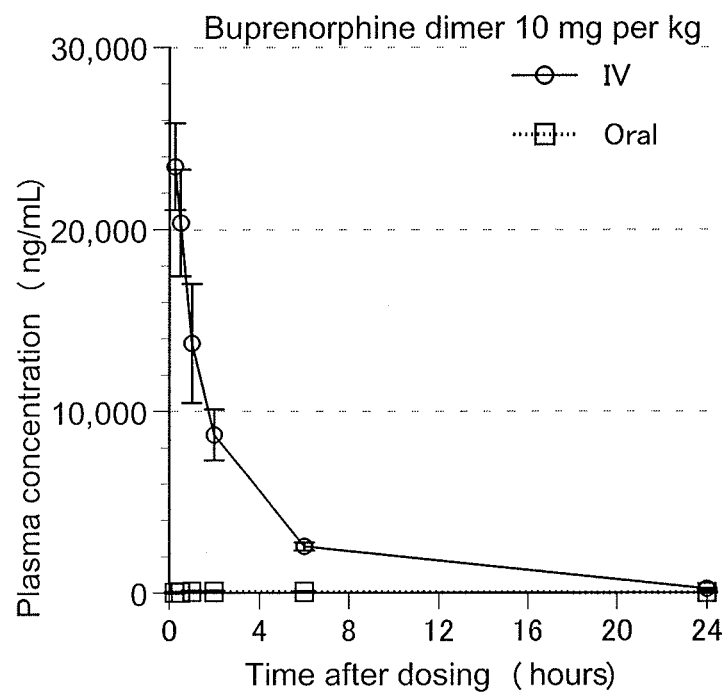
FIG. 7 provides the results of oral and IV bioavailability for buprenorphine and the buprenorphine dimer.

Results: FIG. 7 depicts the plasma concentration profiles of the buprenorphine dimer after 10 mg oral and IV dose. The graph indicates that the absolute bioavailability, measured as a ratio of the area under the concentration curve after oral and IV dose, of the dimer was 1% or less, where as that of the monomer was about 30%.

Example 7

In Vivo Assay: Stress-Induced Fecal Output

Figure 8:
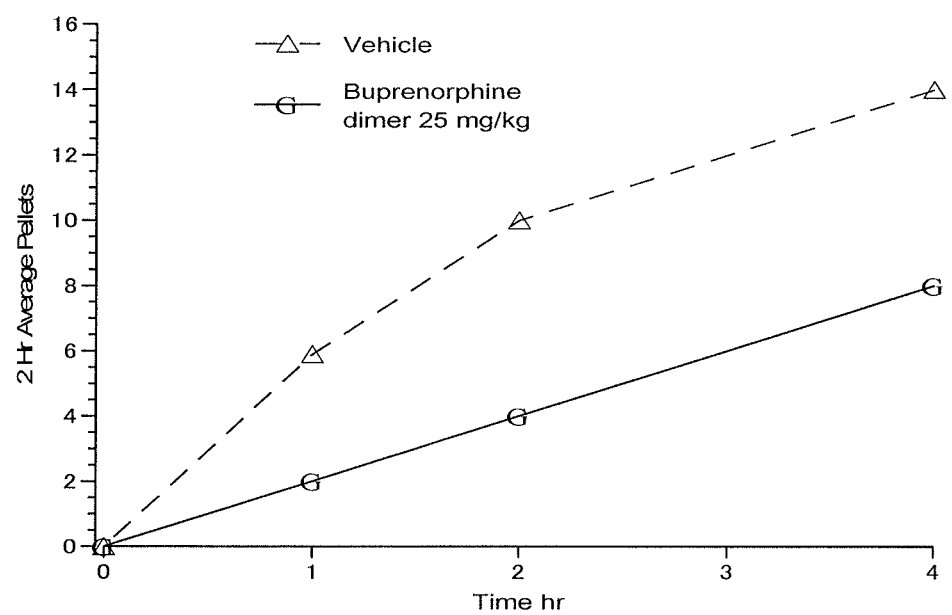
FIGS. 8 and 9 provide the graphs for stress-induced fecal output of male CD-1 mice according to the evaluation of Example 7.
Figure 9:
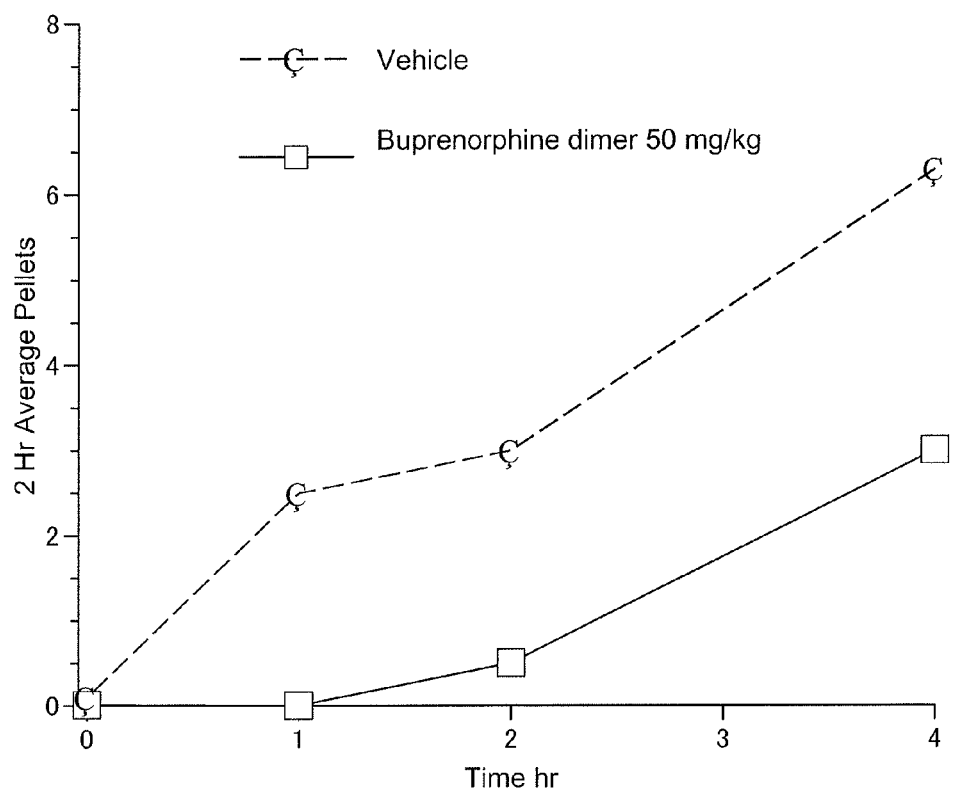
Figure 10:
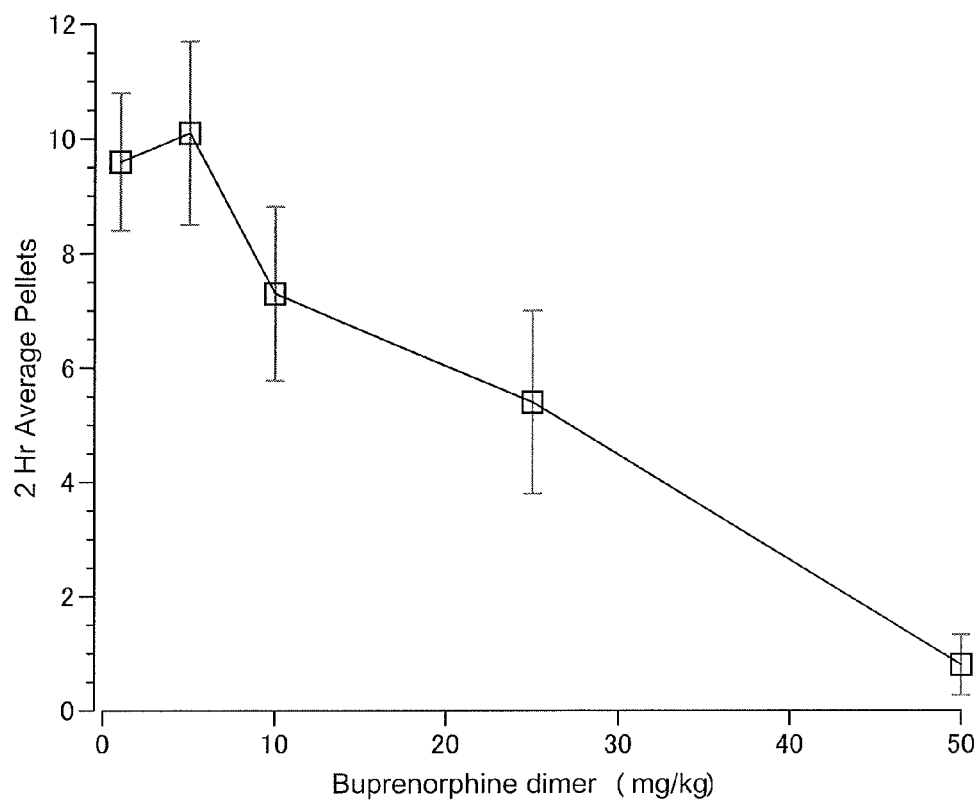
FIG. 10 demonstrates that buprenorphine dimer decreases fecal output in a dose-dependent manner.

The animals used in the studies are male CD-1 mice, average weight about 30 to 35 g, with an average of 5 mice per dose group. The mice were generally housed in colony housing where they are housed 3 per cage in polycarbonate cages with access to food and water ad lib. On the day of the experiment they are transported to the procedure room where they were individually housed in 20 cm wide×20 cm deep×15 cm tall cages, equipped with a wire mesh bottom after intragastric administration of test compound. During the test the animals were allowed access to water ad lib. The wire mesh bottomed tall cage creates a novel environment which induces stress in mice. The number of pellets excreted was determined on hourly basis. Results are shown in FIG. 8-10.

Results: FIGS. 8 and 9 show that oral doses of the buprenorphine dimer significantly reduced the fecal output in mice versus placebo (vehicle). The doses investigated were 25 and 50 mg per kg. The results did not change even when the animals with zero fecal output, suggesting extreme sensitivity, were removed from the analysis. FIG. 10 shows that fecal output in mice decreases with dose, which indicates a true pharmacological effect.

In Vivo Assay: Effect on Post-Inflammatory Altered GI Transit Time

This test was designed to measure the effect of test substance on gastrointestinal hypersensitivity that occurs following inflammation. Post-inflammatory altered GI transit was induced in male CD-1 mice by injecting freshly opened oil of mustard (95% pure allyl isothiocyanate, 0.5% in ethanol). The effect of stress on GI is motility is evaluated 3 to 4 weeks later, when although there is no longer inflammation, the GI tract remains in a hypersensitive state. Effect of test substance was measured after oral administration (intragastric gavage) and subjecting the animals to environmental stress by housing them in a 20 cm wide×20 cm deep×15 cm tall cages, equipped with a wire mesh bottom. During the test, the animals were allowed access to water ad lib. The wire mesh bottomed tall cage creates a novel environment, which induces stress in mice. The number of pellets excreted was determined on hourly to two-hourly basis. See FIG. 11.

Figure 11:
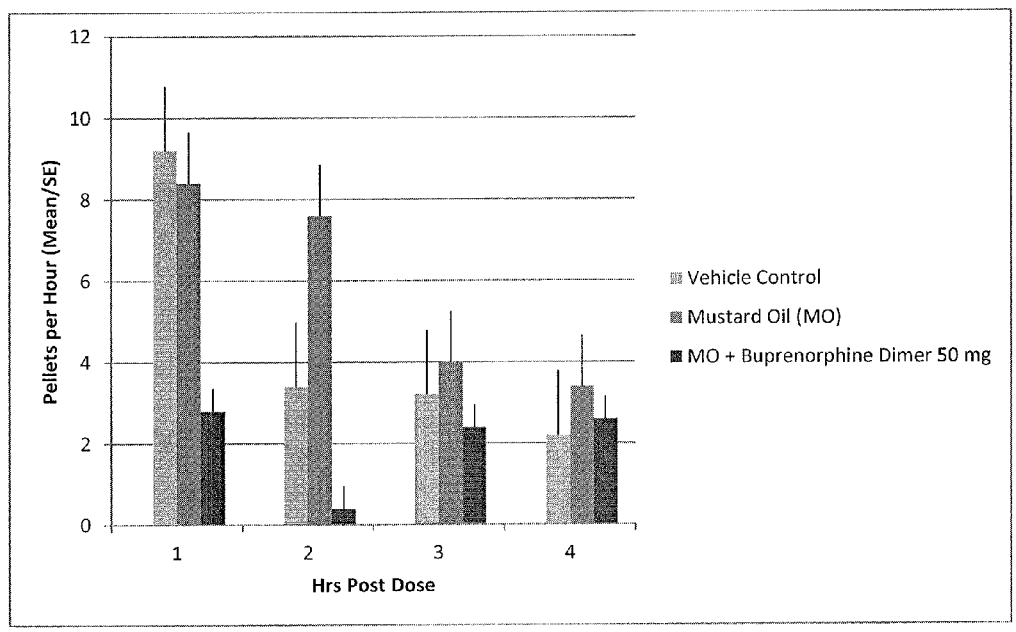
FIG. 11 shows the effect of buprenorphine dimer on gastrointestinal motility in post inflammatory models according to Example 7.

As shown in FIG. 11, the buprenorphine dimer at 25 mg per kg significantly decreased gastrointestinal motility, as measured by fecal output in post-inflammatory models. The graph also shows the increase in fecal output in the mice not treated with mustard oil was transient and did not last beyond 1 hour. The increased fecal output in mustard oil treated animals persisted even at 2 hours. The dimer continued to control gastrointestinal motility even at 2 hours and results were statistically significant.

It is understood that the examples and embodiments described herein are for illustrative purposes only and that various modifications or changes in light thereof will be suggested to persons skilled in the art and are to be included within the spirit and purview of this application and scope of the appended claims. To the extent there is conflict between the priority applications and the present application, any inconsistencies are to be resolved in favor of the present application. All publications and patents cited herein are hereby incorporated by reference in their entirety for all purposes.

What is claimed is:

1. A buprenorphine dimer compound having Formula (I):

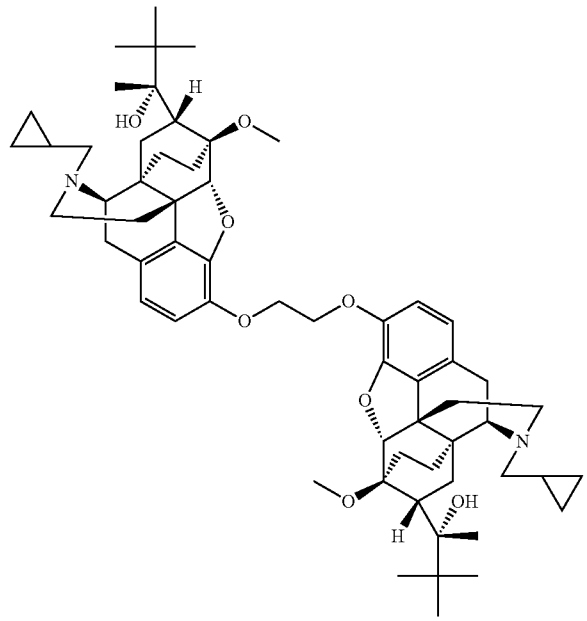

Formula (I)

or a pharmaceutically acceptable salt or solvate thereof.

2. The buprenorphine dimer compound of claim 1, wherein the compound is in the form of a pharmaceutically acceptable salt.

3. A pharmaceutical composition comprising a pharmaceutically acceptable carrier or excipient and a buprenorphine dimer compound of claim 1.

4. A method of treating or managing gastrointestinal hyperalgesia wherein
the method comprises administering to a patient in need thereof a therapeutically effective amount of a buprenorphine dimer compound of claim 1.

5. A method of treating IBS-D in a patient in need thereof, said method comprising administering to said patient a therapeutically effective amount of a buprenorphine dimer compound of claim 1.

6. A method in accordance with claim 5, wherein the patient is a human and wherein the dose administered is about 0.1 mg/kg of the patient's body weight to about 7.2 mg/kg of the patient's body weight.

7. A method in accordance with claim 5, wherein the patient is a human and wherein the dose administered is about 10 to about 50 mg daily.

8. A citric acid salt of the compound of claim 1.

9. A method according to claim 5, wherein the compound is administered as a citric acid salt.

* * * * *